United States Patent [19]

Maarschalkerweerd

[11] Patent Number: 4,482,809
[45] Date of Patent: Nov. 13, 1984

[54] ULTRAVIOLET FLUID PURIFYING DEVICE

[75] Inventor: Jan M. Maarschalkerweerd, London, Canada

[73] Assignee: Trojan Technologies Inc., London, Canada

[21] Appl. No.: 611,912

[22] Filed: May 18, 1984

Related U.S. Application Data

[63] Continuation of Ser. No. 382,146, May 26, 1982, abandoned.

[30] Foreign Application Priority Data

Nov. 30, 1981 [CA] Canada .................................. 391198

[51] Int. Cl.$^3$ ......................... G01N 21/01; A61L 2/10
[52] U.S. Cl. ..................................... 250/436; 250/435; 422/24
[58] Field of Search .......................... 250/432, 436, 437

[56]  References Cited

U.S. PATENT DOCUMENTS

| | | | |
|---|---|---|---|
| 3,462,597 | 8/1969 | Young | 422/2 X |
| 3,948,772 | 4/1976 | Ellner | 422/2 X |
| 4,255,663 | 3/1981 | Lewis | 250/436 |
| 4,367,410 | 1/1983 | Wood | 250/436 |
| 4,400,270 | 8/1983 | Hillman | 250/436 |

Primary Examiner—Bruce C. Anderson
Attorney, Agent, or Firm—Frishauf, Holtz, Goodman & Woodward

[57] ABSTRACT

For ultraviolet purification or sterilization of fluids, particularly waste water, lamp sections, each composed of opposed pairs of fluid impermeable light unit receiving sockets and lamp units therebetween are provided. Each lamp section consists of an inner, elongate, cylindrical ultraviolet ray emitting lamp and an outer, coaxial and substantially co-extensive cylindrical sleeve, arranged in parallel rows. Due to its immersion capability, the array of rows of lamps can be fluid immersed in either an open or closed system. Moreover, lamp withdrawal, fluid impermeable closure means is provided on at least one of each pair of sockets to facilitate lamp withdrawal in the event of burnout. Each row of lamps can also be modularized to facilitate easy removal of a malfunctioning row of lamps without having to shut down or remove the entire device from its fluid environment.

10 Claims, 3 Drawing Figures

ULTRAVIOLET FLUID PURIFYING DEVICE

This application is a continuation, of application Ser. No. 382,146, filed May 26, 1982 abandoned.

This invention relates to an ultraviolet fluid purification or sterilization device particularly for immersion in waste water.

BACKGROUND

The ability of ultraviolet light to kill of destroy micro-organisms in air or liquid is well known. Ultraviolet light has successfully been employed as a purifying or sterilizing technique in both domestic and small-scale industrial applications. Its germicidal qualities, however, in any given application, depends in part upon the intensity of the ultraviolet light, the fluid exposure time to the light and the light transmission quality of the fluid itself. There has been a recent trend towards "thin film" ultraviolet radiation whereby a thin film or layer of the fluid to be purified is constrained to pass in close proximity to an elongate ultraviolet ray emitting source which itself is normally covered or surrounded by a protective quartz jacket or sleeve. The thin film passage of the fluid may be in a direction which parallels the elongate axis of the ultraviolet lamp as disclosed, for example, in Canadian Pat. No. 1,062,437-Lewis, issued Sept. 18, 1979 or perpendicular thereto as disclosed, for example, in U.S. Pat. No. 3,837,800-Wood, issued Sept. 24, 1974. Both of these thin film ultraviolet purifying or sterilizing designs are intended for use in a closed fluid supply system wherein the fluid which is in close proximity to the lamp units does not contact the lamp ends and their attendant electrical interconnection with a source of electric power. In other words, the free ends of the ultraviolet lamps witin its associated sleeve or jacket of a closed system are not designed to be themselves immersed in water although removal and replacement of burned out lamps can be a relatively simple task. In addition to their inability to be water immersed, these known thin-film closed ultraviolet purification systems are relatively costly to manufacture and individually limited in handling many industrial fluid throughout requirements found in existing water purification plants and waste water treatment facilities. Moreover, whether or not ultraviolet irradiation is achieved using the thin-film principle, closed systems are not readily adaptable and installed in existing water or effluent facilities where the fluid to be treated flows through open containment streams, channels, sluices or the like.

BRIEF SUMMARY OF INVENTION

The novel ultraviolet purification or sterilization device of this invention is so designed that all lamp sections comprising elongate lamp units and their associated lamp unit receiving sockets can be totally water immersed yet permit ready withdrawal and removal of a lamp in the lamp unit in the event of burn-out. Further, the novel device can be used in either a closed or open system as above described and if desired, the array of parallel lamp sections can be positioned sufficiently close to one another in order to take advantage of the thin-film treatment principle when either the axes of the light units extend in a direction parallel to the fluid flow or are normal to this fluid flow.

In accordance with yet another aspect of this invention, each row of the parallel rows of spaced apart and parallel lamp sections which themselves each include a lamp unit and its end pair of water impermiable lamp unit receiving sockets can be modularized. This permits the ready withdrawal and replacement of one row of lamp sections as a modular unit independently of the others which can remain operational; removal and replacement being normally undertaken where one or more lamps in the module has burned-out.

Another feature of this invention resulting from modularizing each row of fluid immersible lamp sections, is that the number of required rows needed for any given open system application can be readily met merely by adding or subtracting one or more of the modules. Thus, for a given width of a containment stream in which the lamp sections are to be positioned in a direction parallel to the flow, the required number of rows can be readily predetermined. Where the lamp sections are at right angles to the fluid flow direction, additional modules can be added to either the upstream or downstream ends of the device. Transverse modular additions would normally take place in situations where additional ultraviolet irradiation is required in order to ensure full and complete germicidal irradiation. It will also be apparent that this desired result can also be achieved by separately locating two or more devices in the same fluid stream. Further, it is also possible to arrange the axes of the lamp sections in one device parallel to the stream flow whilst the lamp section axes of the other device is in a perpendicular relationship. The number and spacing between the lamp sections in each row can also be increased or decreased to meet the germicidal dictates for any given installation and the cross-sectional configuration (e.g. depth) of the containment stream in which the lamp sections are immersed.

The present invention can be described in general terms as an ultraviolet purifying device comprising a supporting frame, parallel rows of spaced apart and parallel lamp sections wherein each of said lamp sections includes a pair of opposed, fluid impermeable lamp unit receiving sockets and a lamp unit which extends therebetween. Each said lamp unit itself comprises an inner, elongate, cylindrical ultraviolet ray emitting lamp and an outer co-axil and substantially co-extensive cylindrical sleeve. There is also provided means for supporting said lamp sections in each row in spaced apart relationship, electrical conductor means for said lamps and lamp withdrawal fluid impermeable closure means on at least one of each pair of said sockets.

As indicated above, and if desired, the novel device can be modularized by the inclusion of means for separately withdrawing one row of said lamp sections from the remaining rows of said lamp sections. Accordingly, and with regard to this modular feature, the novel device can also be generally described as a ultraviolet fluid purifying device which has a support frame and a plurality of separately removable fluid immersable ultraviolet lamp modules which are positioned thereon and wherein each module includes a pair of opposed, spaced apart and parallel lamp unit supporting leg sections; opposed and equally spaced apart pairs of fluid impermeable lamp unit receiving sockets on said leg sections; lamp units which are supported by and which extend between each pair of said lamp unit receiving sockets; each lamp unit comprising an ultraviolet ray emitting lamp and its associated jacket as previously described; electrical contact means included in each of said sockets which are in electrical engagement with said lamps and, like before, at least one socket in each of said socket pairs at its end remote from said lamp unit including lamp withdrawal fluid impermeable closure means.

Advantageously, the means for supporting the lamp sections or in the modular configuration, the supporting leg sections can be constructed from hollow conduit. Additionally, an upper frame section also composed of hollow conduit can extend above and communicate with the hollow leg sections and thereby internally carry the electrical conductor leads for the electrical contact means included in the sockets for the lamps. Moreover, these leads on the upper frame can all commonly terminate in an electrical connector means which electrically couples the module to a remote power supply. The upper frame itself can conveniently function as a module withdrawal means as it need only be hand grasped and pulled out. A reflector plate used to reflect back ultraviolet light and protect operating personnel from ultraviolet light can also be positioned above the lamp sections or lamp units in each module and can be conveniently carried by the same means which supports the lamp sections.

The spacing between lamp sections or lamp units in each row normally but not necessarily should be uniform with the selected spacing ideally predetermined in order to meet the germicidal conditions in which it will operate. Further, it will also be appreciated that neighbouring lamp sections or lamp units in each row may be parallel or diagonally offset; the latter configuration producing the tightest packing of the array of lamp units or lamp sections.

BRIEF DESCRIPTION OF DRAWINGS

In the accompanying drawings which illustrate one working embodiment of this invention.

DETAILED DESCRIPTION OF DRAWINGS

Figure 1:
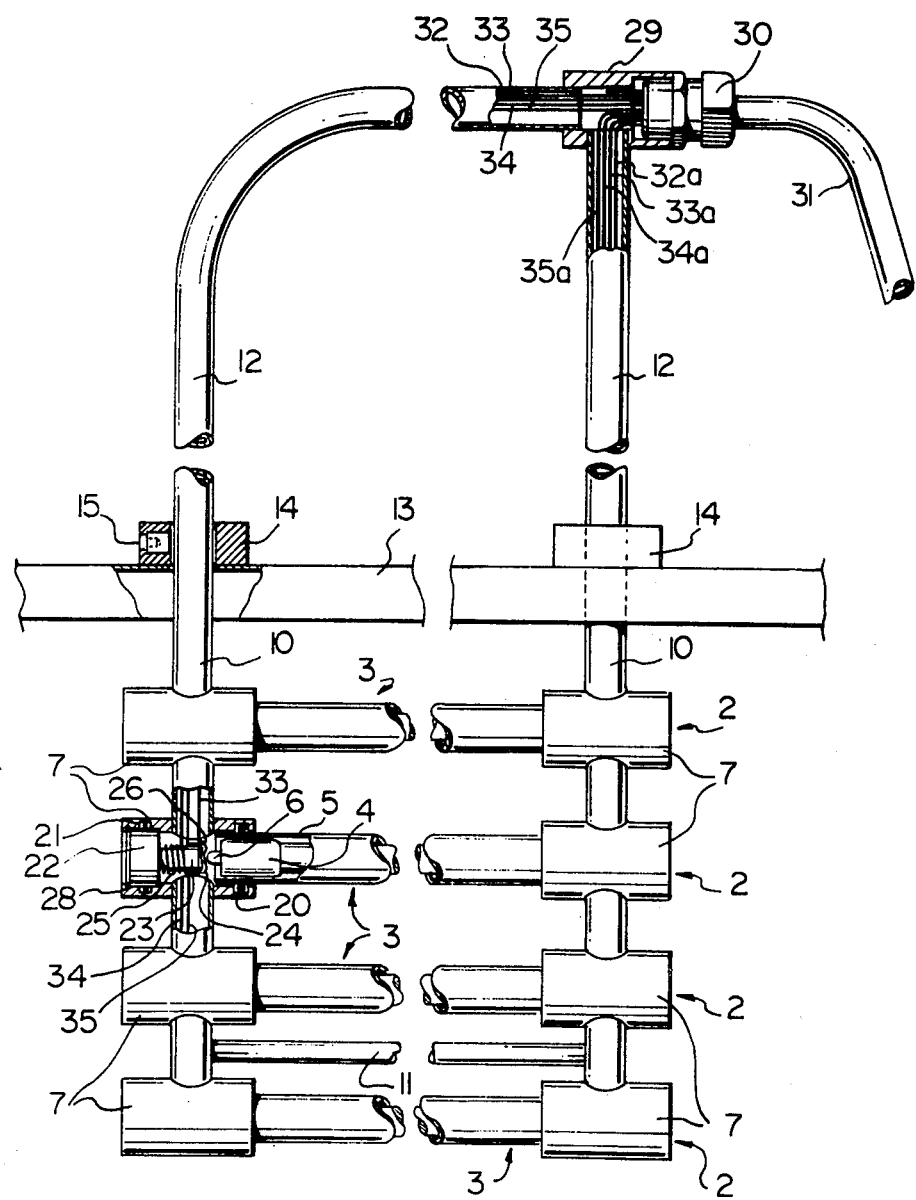
FIG. 1 is a side view of an operating module illustrating the lamp sections, reflector plate and upper frame section and also showing internal detail in partial cutaway.

For ease of understanding, the same reference numerals have been used in the drawings to depict similar component parts.

Referring to FIG. 1, the ultraviolet fluid sterilization or purification module therein illustrated is generally indicated by reference numeral 1. A plurality of equally spaced apart and parallel lamp sections 2 are arranged in a vertical row as shown. These lamp sections each include lamp units 3 which have an inner, elongate, cylindrical ultraviolet ray emitting lamp 4. A typical lamp suitable for this purpose is one available from Voltarc Inc. of U.S.A., which is a slim line single pin lamp sold under Model G36T6L. Surrounding lamp 4 is an outer, coaxial and substantially co-extensive cylindrical jacket or sleeve 5 which protects lamp 4 while permitting the transmittance of the ultraviolet rays therethrough. The particular lamp 4 illustrated is provided with a single pin contact 6 at either of its ends (only one being shown in FIG. 1).

Each of the lamp units 3 at its ends terminates in pairs of opposed fluid impermeable lamp unit receiving sockets 7. As discussed in greater detail below, this arrangement permits full fluid immersion of all of the lamp sections with included lamps 4 interior thereof remaining dry. Lamp section supporting means or leg sections 10 support and interconnect the lamp sections in spaced relationship. As best seen in FIG. 1, an optional crossbrace 11 can interconnect legs 10 at their lower extremities in order to impart further strength to the module and relieve pressure upon lamp units 3. The legs 10 can be made up of hollow conduit which interconnects the numerous sockets 7 and as illustrated, can extend above the upper most of the lamp sections in a module so as to interconnect the two legs by means of upper frame section 12. An inverted U-shaped elongate channel or reflector component 13 is positioned intermediate upper frame 12 and the upper lamp section 2. Collar 14 and set screw 15 which are attached to reflector 13 serves to fixedly secure the reflector above and parallel to the lamp sections and also impart further structural rigidity to the module. Reflector 13 serves the three-fold purpose of reflecting back rays emitted from the lamp sections, protecting service or maintenance personnel operating in the vicinity of the device and supporting the device in the frame.

With particular reference to the cross-sectional detail of the socket 7 depicted in FIG. 1, the socket at its end adjacent lamp unit 3 is provided with fluid tight circular sealing gasket 20. Lamp withdrawal fluid impermeable closure means is also provided at the other end of socket 7 and in the specific embodiment illustrated, includes end plug 22 and plug protrusion 23. Fluid sealing gasket 21 is disposed between plug 22 and socket 7 so that the interior of the socket remains dry. Exterior of plug 22 and serving to hold it in position is snap washer 28.

Since the illustrated lamps 4 have single contact pins 6 at either of their ends, four electrical leads 32, 33, 34 and 35 are lead down the interior of one leg 10 (the left hand leg of FIG. 1) and the corresponding complementary electrical contact leads 32a, 33a, 34a and 35a lead down the other leg and terminate at their complimentary lamp sections of the four lamp sections illustrated. As best seen in the cross-sectional detail of FIG. 1, protrusion 23 at its free end carries metalized strip or clip 24 which is biased away from plug 22 by means of spring 25 and towards contact pin 6. As illustrated, lead 33 terminates in electrical abutting contact with clip 24 at 26. It will be evident that upon removal of washer 28 and plug 22 with spring 25 and clip 24, that lamp 4 can be withdrawn outwardly of jacket or sleeve 5 through the open end of socket 7. While not shown in FIG. 1, the opposite socket to the socket shown in cross-section can be constructed in an identical manner and in which case the contact lead would be lead 33a. It will be also apparent, however, that the free end of this socket can be permanently sealed so that the lamp 4 can only be withdrawn from one end of each pair of opposed sockets.

The other or upper ends of the leads terminate in electrical connector 29 in a known manner and as illustrated, are electrically inter-connected to power cord 31 by complimentary male connector 30. The module thus, if desired, can be readily separated from its power supply merely by withdrawing male connector 30 at this point.

Figure 2:
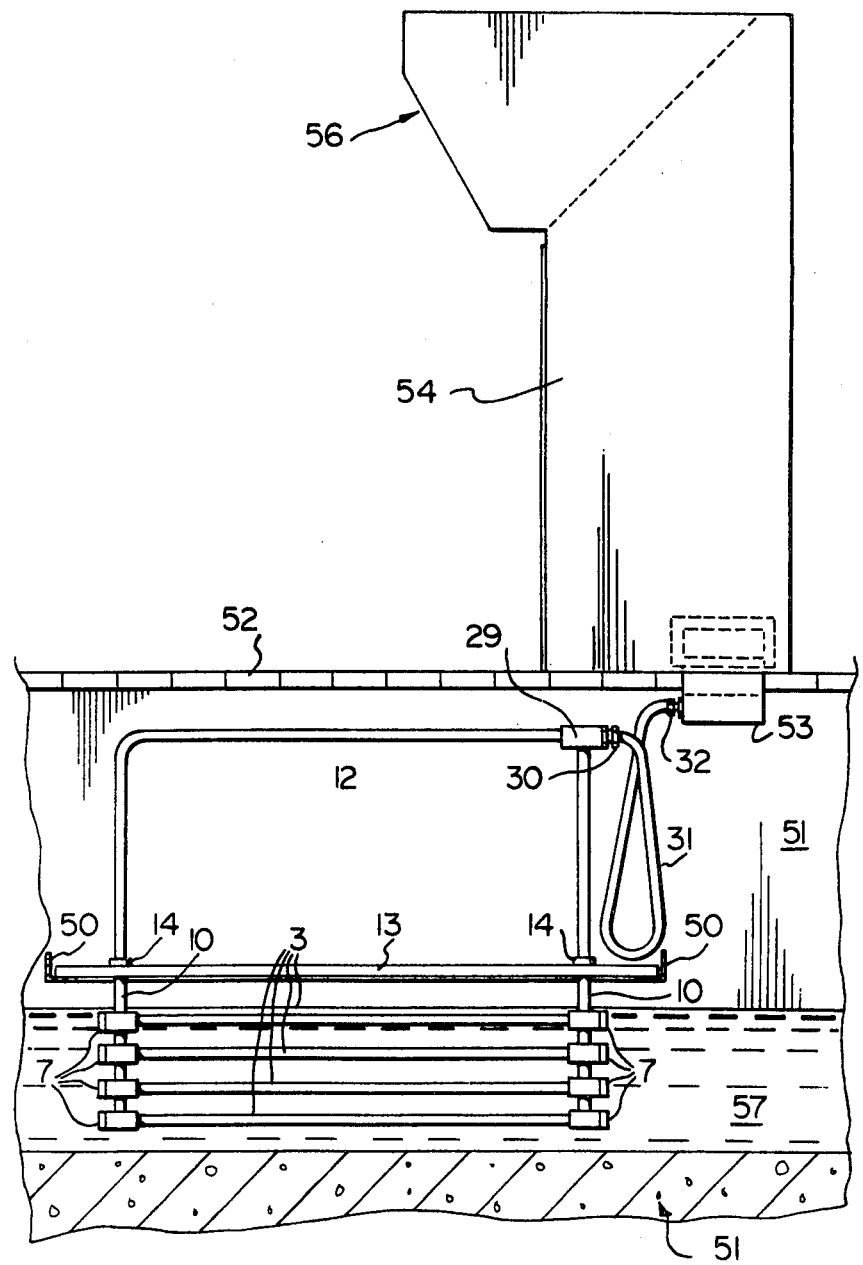
FIG. 2 is a similar view to that of FIG. 1 illustrating a module when positioned in a effluent channel and when connected to its electrical control panel.
Figure 3:
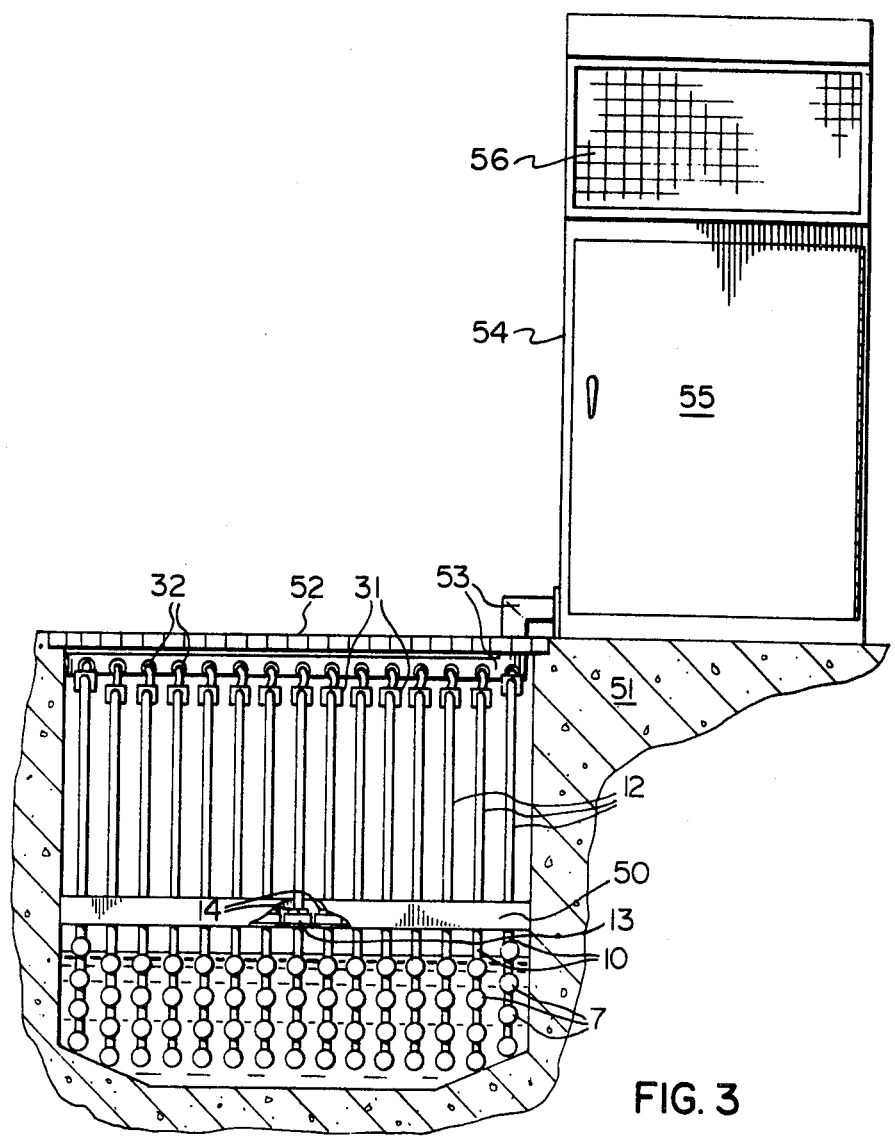
FIG. 3 is an end view of the operational device of FIG. 2 but now illustrating a plurality of modules with lamp sections arranged in a direction parallel to the fluid flow.

FIGS. 2 and 3 illustrate one typical open system installation of the device consisting of a number of modular and removable units. As shown, lamp sections 2 are disposed below fluid 57 in an open containment channel 21 and arranged so that their axial alignment parallels the fluid flow direction. The lamp sections in each module are supported in position by means of reflectors 13 which themselves at their free ends are supported by frame members 50 which are transverse of the channel. The upper surface of the channel is covered by safety grid 52. Adjacent the side of the channel is a control box and power supply 54 having access door 55 and display 56 as discussed below. Electrical distribution conduit 53 extends from the control box 54 and across the open channel. Cables 31 for each of the modules are connected to corresponding leads (not shown) within the conduit and control box and are individually connected by means of male connecters 32. It will thus be apparent that individual modules can be disconnected either at connecter 30 or 32 and vertically removed from the remainder of the array of lamp sections.

Display panel 56, if employed, advantageously can include a grid pattern of lights or signals which corresponds in number and array pattern to the configuration of the lamp units in the operating device. As each light or signalling device in the display panel is dedicated to and forms part of the electrical circuit for each of the numerous lamp sections, should one lamp in a module burn out, the particular module and the specific burned out lamp can be readily and conveniently visually determined upon checking the display grid.

Because the modules can be quickly and readily removed and replaced, the lamp sections in each module, upon withdrawal, can be cleansed in a matter of seconds or minutes. Thus, the need for cumbersome lamp "wipers" as known in the art is not required.

It will be appreciated that variations to the construction of the specifically disclosed lamp section assembly having means permitting fluid sealed lamp withdrawal means can be made without departing from the spirit or scope of this invention. Similarly, variations or alterations to the construction of the modular units as herein specifically disclosed can also be made falling within the overall inventive concept as elsewhere presented in this disclosure.

I claim:

1. An ultraviolet light waste water purifying device comprising
   a support frame;
   a plurality of separately removable fluid immersible ultraviolet lamp modules supported on the frame, each of the said modules including:
   a pair of opposed, spaced apart and parallel hollow leg sections (10);
   a plurality of pairs of fluid impermeable lamp unit receiving sockets (7) fluid tightly secured to said leg sections (10), the sockets of the pairs being in alignmment to receive the lamps, and the pairs being longitudinally staggered along the leg sections to permit placement of a plurality of lamps (4) in any one module;
   the lamp units (3) being supported by and extending between each pair of said lamp unit receiving sockets (7), each of said lamp units (3) comprising an inner, elongate, cylindrical ultraviolet ray emitting lamp (4) and an outer, co-axial and substantially co-extensive ultraviolet light transmissive cylindrical jacket (5) surrounding said lamp (4);
   means (20) for sealing the outer cylindrical jacket (5) into aligned, opposed sockets forming a pair;
   electrical contact means (24) included in each of said sockets (7) which are in electrical engagement with said lamps (4),
   at least one socket (7) in each of said socket pairs at its end remote from said lamp unit including lamp access means collinear with the lamp (4); and
   removable fluid impermeable closure means (28, 22) sealing the access means into the respective socket to permit individual withdrawal of a lamp from the respective socket.

2. The device as claimed in claim 1, wherein each of said modules (FIG. 1) further includes an elongate reflector plate (13) positioned above and parallel to said lamp units (3).

3. The device as claimed in claim 2, wherein each of said modules (FIG. 1) further includes an upper frame section (12) positioned above said leg sections (10) and said reflector plate (13) and which interconnects said leg sections (10).

4. The device as claimed in claim 3, wherein said leg sections (10) and upper frame section (12) comprise hollow intercommunicating conduit sections (10, 12).

5. The device as claimed in claim 4, wherein said electrical contact means (24) further includes electrical conductor leads (32, 33, 34, 35) interior of said conduit sections (10, 12).

6. The device as claimed in claim 1, wherein each of the said modules (FIG. 1) is arranged so that the spacing between two adjacent lamp units (3) in one module is approximately equal to the spacing between a lamp unit (3) of said one module and a lamp unit (3) of the next adjacent module.

7. The device as claimed in claim 1, further including electrical connector means (32, 33, 34, 35) for separately connecting each of said modules to a remote power supply (54).

8. The device as claimed in claim 1, wherein the lamp units (3) in each module are positioned on said support frame in a direction parallel to a flow direction of said fluid.

9. An ultraviolet light waste water purifying device comprising a frame (10,12, 13, 50),
   parallel rows of spaced apart lamp sections,
   each of said lamp sections including a fluid-tight assembly of a pair of hollow, tubular spaced apart and parallel legs and opposed fluid impermeable lamp unit receiving sockets (7) longitudinally staggered along the legs, said sockets having a lamp unit (3) extending therebetween,
   each of said lamp units (3) comprising an inner, elongate, cylindrical ultraviolet ray emitting lamp (4) and an outer, co-axial and substantially co-extensive ultraviolet light transmissive cylindrical sleeve (5),
   means for supporting each said lamp unit (3) in each of said lamp sections in spaced apart relationship (10, 12),
   electrical conductor means (32, 33, 34, 35) for said lamps (4), and
   lamp access means collinear with the lamps comprising fluid impermeable closure means (28, 22) on at least one socket of each pair of said sockets (7);
   and wherein the outer ultraviolet light transmissive cylindrical sleeves (5) of each of the lamp units (3) is sealed to the respective sockets (7) between which the units (3) extend, to permit total immersion of the lamp sections including said legs and sockets in waste water to be purified.

10. The device as claimed in claim 9 further including means (12) for separately withdrawing one row of said lamp sections (FIG. 3) from the remaining rows (FIG. 3) of said lamp sections (FIG. 3).

* * * * *